United States Patent [19]
de Vries

[11] Patent Number: 6,001,773
[45] Date of Patent: Dec. 14, 1999

[54] SPROUT INHIBITING AND/OR ANTI-FUNGAL COMPOSITION FOR POTATOES

[75] Inventor: Robert G. de Vries, Apeldoorn, Netherlands

[73] Assignee: Luxan B.V., Elst, Netherlands

[21] Appl. No.: 09/014,162

[22] Filed: Jan. 27, 1998

[30] Foreign Application Priority Data

Jan. 27, 1997 [NL] Netherlands ............................ 1005100

[51] Int. Cl.⁶ ............................ A01N 35/00; A01N 43/50
[52] U.S. Cl. ......................... 504/118; 504/139; 504/275; 504/348; 514/399; 514/690
[58] Field of Search ................................ 514/399, 690; 504/118, 139, 275, 348

[56] References Cited

U.S. PATENT DOCUMENTS 3,787,566  1/1974  Gauvreau .................................. 424/45

FOREIGN PATENT DOCUMENTS 195 23 320 A1  1/1997  Germany .
WO 95/09536  4/1995  WIPO .
WO 95/12311  5/1995  WIPO .

OTHER PUBLICATIONS

Tomlin, The Pesticide Manual, pp. 580–581, (1995).
"Azoxystrobin Compoitions", Research Disclosure, No. 390, Oct. 1996, pp. 673–674 XP000639940.
"Suppression of Sprouting in Stored Potatoes by Volatile Organic Compounds", D.F. Meigh, J. Sci Fd Agric., Mar. 1969, vol. 20, pp. 159–164.
Chemical Abstract, "Experiments on the Control of Potato Tuber Rotting by Fusarium Coeruleum", D. Bommer et al., abstract No. 101538, Columbus, Ohio, Oct. 29, 1973 & Landbauforsch, Voelkenrode, vol. 22, No. 2, 1972, pp. 123–128.

*Primary Examiner*—Allen J. Robinson
*Attorney, Agent, or Firm*—Evenson, McKeown, Edwards & Lenahan, PLLC

[57] ABSTRACT

In order to reduce the amount of synthetic fungicides used in the storage of potatoes, a method of repelling fungi in potatoes as effectively as possible has been looked for. What has also been looked for is an agent that is effective both for repelling fungi and for inhibiting sprouting in the storage of potatoes. It has been found that a combination of carvone and one or more fungicides leads to a synergistic effect both for repelling fungi and for inhibiting sprouting.

10 Claims, 3 Drawing Sheets

SPROUT INHIBITING AND/OR ANTI-FUNGAL COMPOSITION FOR POTATOES

BACKGROUND AND SUMMARY OF THE INVENTION

This invention relates to a sprout inhibiting and/or anti-fungal composition for potatoes.

Sprouting, also referred to as shooting, Is a problem in the storage of potatoes. It leads to a potato quality loss as a result of lose of weight. Further, the turgor of the potatoes lessens (the potatoes become softer), and toxic products may be formed in the sprouts.

Sprouting can be inhibited by storing the potatoes at a temperature of 2° C., but at such a low temperature reducing sugars are formed which give the potatoes, when (deep) fried, a brown color and cause them to taste sweet (Maillard reaction). For this reason the potatoes are typically stored at a temperature between 5 and 8° C. At such a temperature the problem of the formation of reducing sugars is absent or considerably smaller, but upon prolonged storage sprouting is not entirely prevented.

Therefore, sprout inhibiting agents are necessary to maintain potato quality during storage, both in potatoes intended for direct consumption and in potatoes to be processed into potato products. Such sprouting inhibitors are used to inhibit sprouting over prolonged storage periods at lower temperatures, i.e., below 10° C.

For over two decades now, chemical sprouting inhibitors have been successfully utilized to prevent sprouting or shooting during the storage of potatoes. Propham (IPC) and chlorpropham (CIPC), which were originally developed as herbicides, are utilized as sprout inhibitors on a large scale in Europe, while in America also maleic acid anhydride is used. In England, tecnazene is still being used as a sprout inhibitor.

These last two agents are probably going to be forbidden in the near future. The use of IPC will no longer be permitted in the EU as of April 1997. Also, the market for ecologically grown potatoes, that is, untreated potatoes or potatoes treated with as little chemical agent as possible, is rapidly expanding.

In international patent application WO-A-95/09536 it is proposed inter alia to control potato sprouting with a mixture of menthol and carvone. Carvone is a compound which is present in the essential oil of the seeds of the caraway plant (Carum carvi). This compound is of interest because it is registered as a food additive and has the so-called "GRAS" status (Generally Recognized As Safe). Moreover, it is possible to grow caraway on a commercial scale. This is already happening on a large scale in various countries both inside and outside Europe.

Sprouting, however, is not the only problem in the storage of potatoes. Attack of the potatoes by fungi is also an important obstacle. Fungi primarily lead to loss of potato quality inter alia in that the taste is affected. In a later stage, diseases, such as silver scurf, and even decay of the potatoes may occur. An the potatoes constitute an excellent nutrient medium for the fungi, theme reproduce rapidly, Thus a complete stock of potatoes may be lost through a minor attack of only a few potatoes. As the process involved here is irreversible, it is of great importance that fungi be repelled from the very outset.

For repelling fungi in potatoes, at present a wide range of synthetic control agents are used. These, however, must be applied in considerable amounts in order to accomplish an adequate effect. The necessity of such large amounts of synthetic fungicides not only entails substantial costs, but is also undesirable in view of the associated environmental effects.

What has accordingly been searched for is a method of repelling fungi in potatoes in a manner as effective as possible, while the amount of required synthetic agents is considerably reduced. What has also been searched for is an agent that is effective both in repelling fungi and in inhibiting potato sprouting.

Surprisingly, it has now been found that a combination of carvone and one or more fungicides leads to a synergistic effect both for repelling fungi and for inhibiting sprouting. It has been found that when potatoes are treated with a combination of carvone and one or more fungicides, fungi are more effectively repelled.

The sprout inhibiting and/or anti-fungal agent consisting of a combination of carvone and one or more fungicides is suitable for use in ware and starch potatoes. The agent according to the invention can also be used in the storage of seed potatoes, so that sprouting is temporarily inhibited and the development of fungi is counteracted.

The carvone used can be D(S(+))-carvone, but also L(R(−))-carvone or a mixture of D- and L-carvone, and can be of vegetable origin or semivegetable through preparation by chemical conversion from, for instance, citrus waste. D-carvone and L-carvone, when used separately, exhibit an equal amount of action and both can therefore be effectively used, separately as well as in a mixture.

The nature of the fungicides that are used in the composition according to the Invention is not critical and in principle a variety of fungicides can be used. It is preferred, however, to use as fungicide one or more compounds from the classes that are active against Helminthosporium spp., inter alia *Helminthosporium solani,* Phoma spp., inter alia *Phoma exigua* var. *exigua* and/or *Phoma exigua* var. *foveata,* Fusarium spp., inter alia *Fusarium sulphureum, Fusarium solani* and/or *Fusarium solani* var. *ooeruleum,* and/or Phytophthora spp., inter alia *Phytophthora erythroseptica,* as these are the fungi that cause most problems in potatoes. Highly suitable examples of compounds from these classes are imidazoles, such as imazalil and prochloraz, and benzimidazole's, such as carbendazim and thiabendazole, which are known to have a very good action against the fungi and microorganisms mentioned and others occurring in potatoes.

The mutual weight ratio of fungicide to carvone in the composition according to the invention is preferably in the range of 1:1 to 1:10, more preferably in the range of 1;2 to 1;5. The most preferred composition according to the invention contains 50 to 250 grams of imazalil and 400 to 600 grams of carvone per liter.

The composition can be used dry an a powder or granulate which is imparted to the potatoes as the storage space is being filled with them (this is the so-called basic treatment).

Instead of being used as a powder or granulate, the composition according to the invention can also be misted over the potatoes while they are being stored in the storehouse, as a liquid, emulsion, suspension or suspoemulsion, directly or mixed with a small amount of water.

Further, the sprout inhibiting and/or anti-fungal composition can also be contacted with the potatoes at a later stage during the storage period by misting or spraying in the storage space, with the support of fans in that space.

In that case, depending on the desired mode of application, the present composition can also comprise a suitable carrier, suitable solvents, fillers or other agents conventionally present.

Suitable powdered or granular carriers and fillers are starch and starch derivatives, clay, talcum and other silicas, sand, diatomaceous earth, calcium carbonate and calcium sulfate (gypsum) and the various (co)polymers which can be used as carriers.

For making a granulate, an inert carrier can be impregnated with a solution of carvone and fungicide(s).

Further, granules can be sprayed with a mixture of one or more fungicides and carvone.

Suitable for the application of the sprout-inhibiting and/or anti-fungal agent in a liquid form are solvents of mineral origin, including aliphatic or aromatic solvents or mixtures thereof, which may or may not be chlorinated. Examples of these solvents are xylene, dichloromethane, ketones, aldehydes, alcohols such as glycerols (for instance polyethylene glycol), or derivatives or mixtures thereof. It is also possible to use solvents of animal or vegetable origin, such as linseed oil, soy bean oil or derivatives thereof. It is also possible to use mixtures of such solvents of animal, vegetable and mineral origin.

It is further possible to use a paste. Pastes can be formed by adding thickeners, such as, for instance, synthetic or natural polymeric thickeners, to solutions and emulsions of the composition in the above-mentioned solvents.

It is also possible to use the composition in emulsion form. For preparing an emulsion, carvone and fungicides can be mixed in the desired ratio, whereafter an emulsifier and optionally water or a different solvent is added. Another possibility is that water or a solvent is provided with an emulsifier and is then mixed with a mixture of carvone and fungicide (s).

Suitable emulsifying agents for preparing an emulsion are cationic, anionic and non-ionic surface-active substances of animal, vegetable and mineral origin. Examples are Ca-dodecyl benzene sulfonates, nonyl phenol polyglycol ethers, ethoxylated fatty acid alcohols or amines or derivatives or combinations thereof.

The emulsifier or the mixture of emulsifiers is preferably present in an amount of 2–20% by weight, preferably 10–15% by weight, in the total mixture. The eventual emulsion preferably contains between 20 and 50% by weight of sprout inhibiting and/or anti-fungal composition.

The invention further relates to a method for inhibiting sprouting in potatoes and/or repelling fungi, in which potatoes are treated with carvone and one or tore fungicides.

Obviously, in a preferred method the above-discussed sprout inhibiting and/or anti-fungal composition is used. It should be noted, however, that it is also possible, in accordance with the invention, to treat potatoes separately with carvone and one or more fungicides shortly after each other, which, surprisingly, yields the same synergistic effect.

According to a variant, potatoes are first treated with one or more fungicides or a composition of carvone and one or more fungicides and the potatoes are subsequently treated with carvone a few more times. When after a first treatment with fungicide, optionally in combination with carvone, the potatoes are treated with carvone two or more times after successive periods of six weeks, sprouting is found to be controlled particularly efficiently. In a particularly favorable embodiment the potatoes, after the first treatment, are treated with a mixture of carvone and menthol, as is described in International patent application WO-A-95/09536.

It in customary to store potatoes in bulk or in large bins in the storage space, which is mostly insulated. By means of fans, cooler outside air can be passed through the potatoes. Optionally, the (outside) air, before being passed through the potato mass, can additionally be cooled further by means of cooling systems.

Storage outside in a pit, heap or wall, or in a clamp silo is used for starch potatoes at present, but a variant of this can also be used to store ware potatoes, This last, however, is less common.

For the storage of the potatoes, use can also be made of cells or boxes with a volume corresponding to the ventilation capacity.

The bulk potatoes are preferably dried first, stored for a few days at about 15° C. and then cooled in about two weeks to the desired storage temperature to ensure proper wound healing of damaged potatoes. This period of wound healing is necessary to limit microbial attack and weight losses during storage. The wound healing period of the lot takes about 14 days. After the wound healing period, the potatoes are stored at the desired storage temperature, the temperature being regulated through outside air cooling or mechanical cooling.

The desired storage temperature is 2–4° C. for seed-potatoes, 4–6° C. for ware potatoes, 5–8° C. for French fries and dry industry, and 7–10° C. for chips.

After a sprouting dormancy of a few months after harvest, the potato (depending on variety, history and storage method) begins to exhibit an inclination to sprout. In the course of time, this inclination to sprout grows increasingly stronger.

If cooling takes place in a mechanical manner (so that the desired storage temperature can be reached rapidly), the chances of early sprouting are limited already. To inhibit sprouting in optimum manner., subsequently the sprout-inhibiting and/or anti-fungal mixture according to the present invention is applied.

As the risk of infection with fungi in immediate from the start, it is preferred to treat the potatoes with fungicides or the composition of fungicides and carvone already at the time of storing the potatoes in a storehouse or pit.

The so-called basic treatment consists of imparting the sprout-inhibiting and/or anti-fungal agent (in the form of, for instance, powder or granules), for instance on a conveyor which convoys the potatoes to the storage space. It is also possible to spray or atomize the sprout-inhibiting and/or anti-fungal composition over the potatoes (above the conveyor).

It is further possible to pass the composition according to the invention to the storage space via the air ventilation system. For this mode of application, the composition can for instance be atomized or sprayed into the air. For this purpose it is possible to combine a mixture of carvone and one or more fungicides with a gaseous carrier so as to facilitate introduction into the air stream.

The two treatments can also be combined or be performed one after the other.

In all cases, the sprout-inhibiting and/or anti-fungal agents will evaporate to a greater or lesser extent and so all potatoes to be treated will come into contact with the agent.

The application of the sprout-inhibiting and/or anti-fungal composition according to the invention preferably takes place in a manner such that the concentration of carvone and fungicide together in the air of the storage space is between about 2 and 20 $\mu g/l$ air and more particularly between about 5 and 10 $\mu g/l$ air. At values lower than about 5 $\mu g/l$ air, sprouting inhibition will not be guaranteed to a sufficient extent. Higher values than about 20 µg/l air do not lead to longer sprout inhibition and therefore lead only to unduly large amounts of the composition being used.

BRIEF DESCRIPTION OF THE DRAWINGS

Other objects, advantages and novel features of the present invention will become apparent from the following detailed description of the invention when considered in conjunction with the accompanying drawings.

DETAILED DESCRIPTION OF THE PREFERRED EMBODIMENTS

Figure 1:
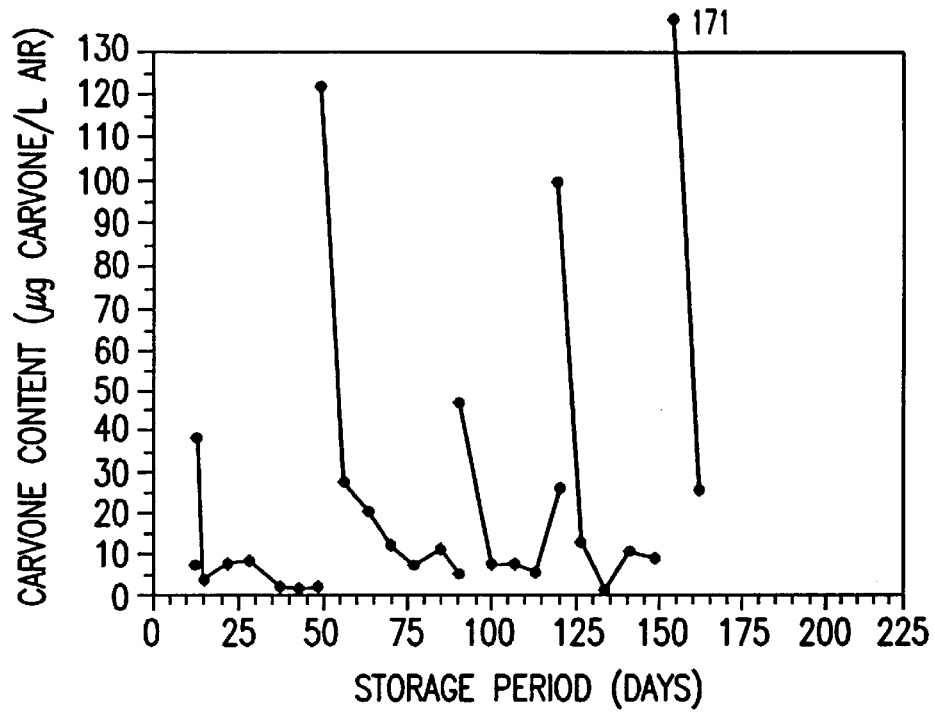
FIG. 1 is a graph showing the carvone content in air against storage period in storage cell 13.

The invention will now be further explained in and by the following Examples.

EXAMPLES

Potatoes

Ware potatoes of the variety Bintje were grown, harvested and stored in a storehouse. The material was stored at about 12° C. for 10 days, followed by sorting whereby in each case about 400 kg in the size 40–60 mm was reserved. A part of the material was intended for silver scurf variants and was stored in bins at about 10° C. until initial provision after 24 days. Another part of the material was intended for Fusaria variants. Until initial provision, after 73 days, this part was stored at about 6° C. A further part was intended for Phoma variants and was stored at about 6° C. until initial provision after 139 days. The separate initial provision for the various storage pathogens occurred for reasons of experimental technique. The potatoes were stored without use of sprout inhibiting agents.

Fungicides

The following fungicidal agents were used.

Talent, contains 95% carvone;

Luxan fungaflor EC, contains 200 grams of imazalil per liter;

D4112 EC 95-1, this formulation contains 500 g of D-carvone per liter;

D4108 EC 95-1, this formulation contains, respectively, 500 g of D carvone +150 g of imazalil per liter;

D4109 EC 95-1, this formulation contains, respectively, 500 g of D carvone +100 g of imazalil per liter.

Storage Duration and Storage Conditions

The potatoes of the different parts as specified hereinabove were stored in eight separate cells. Per part, four repeats were provided. Each repeat comprised 22–24 kg of potatoes and was stored in a bin. The bins were then stored in the different cells according to a lottery scheme. In them, 14–15 tons of potatoes could be stored in bulk. For these tests, the cells had been filled with bins of potatoes for about 5–10%.

To promote the fungal attacks during storage, for silver scurf, *Fusarium solani* var. *coeruleum* and *Fusarium sulphureum* a storage temperature of about 12° C. was aimed for, and for *Phoma exigua* var. *foveata* of about 8° C. In addition, for the silver scurf and *Fusarium solani* var. *coeruleum* a relative humidity (RH) of about 95% was aimed for and for the other fungi an RH of about 90%.

Artificial Damage and Infection with Fungal Spores

In order to be able to control the various kinds of Fusarium fungi and the *Phoma fungus,* the potatoes were first infected with spores of these fungi. Of *Fusarium sulphureum* two species of fungi were available, viz. *Fusarium sulphureum+* (resistant to thiabendazole) and *Fusarium sulphureum–* (not resistant to thiabendazole). The required spores were cultured on dead grains of wheat.

To be able to distribute the spores over the potatoes, the wheat grains were first soaked in water for half an hour. After sieving the suspensions contained, of the two Fusarium species, about 50,000 spores per ml and of the Phoma about 10,000 spores per ml of liquid.

The infection with the different spores was carried out following the above specified storage periods. The spore suspensions were distributed over the potatoes as a fine mist by means of a disk mister (type: Mafex 87A) mounted above a roller conveyor, at a metering position of 39 for the Fusaria and of 40 for the Phoma, using 1 liter of spore liquid per 1000 kg of potatoes to be treated. Immediately prior to the artificial infection (in the same pass), the tubers to be infected were damaged all round. For this purpose, at the end of the loading belt to a roller conveyor, a variable-speed rotary shaft with pins about 15 cm in length had been arranged. From the loading belt, the potatoes dropped onto this rotary shaft with pins and then ended up on the roller conveyor where the artificial infection was carried out.

For inducing silver scurf it was not considered necessary to carry out a prior artificial damaging and infection step. The attack develops spontaneously during warm and humid storage.

The tests involved the following treatments/agents/combinations of agents:

1. Damaged, infected and no protective agent;
2. Damaged, infected and treated at initial provision with Luxan Fungaflor EC, dosage 75 ml/ton of potatoes,
3. Damaged, infected and treated at initial provision with Luxan Fungaflor EC, dosage 112.5 ml/ton of potatoes;
4. Damaged, infected and treated at initial provision with formulation D4112 EC, dosage 100 ml/ton of potatoes, followed by 2× Talent, viz. after 6 and 12 weeks of storage (cells 17, 18, 21 and 28 in connection with different pathogens and times of initial provision);
5. Damaged, infected and treated at initial provision with formulation D4112 EC, dosage 300 ml/ton of potatoes, followed by 2× Talent, viz. after 6 and 12 weeks of storage (cells 17, 18, 21 and 28);
6. Damaged, infected and treated at initial provision with formulation D4112 EC, dosage 100 ml/ton and with Luxan Fungaflor EC, dosage 75 ml/ton of potatoes, followed by 2× Talent, viz. after 6 and 12 weeks of storage (cells 17, 18, 21 and 28);
7. Damaged, infected and treated at initial provision with formulation D4108 EC, dosage 100 ml/ton of potatoes, followed by 2× Talent, viz. after 6 and 12 weeks of storage (cells 17, 18, 21 and 28);
8. Damaged, infected and treated at initial provision with formulation D4108 EC, dosage 150 ml/ton of potatoes, followed by 2× Talent, viz. after 6 and 12 weeks of storage (cells 17, 18, 21 and 28);
9. Damaged, infected and treated at initial provision with formulation D4109 EC, dosage 150 ml/ton of potatoes, followed by 2× Talent, viz. after 6 and 12 weeks of storage (cells 17, 18, 21 and 28);

10. Damaged, infected and treated at initial provision with Luxan Fungaflor EC, dosage 75 ml/ton of potatoes, followed by 3× Talent, viz. within 1 week after initial provision and after 6 and 12 weeks of storage (cells 17, 18, 21 and 28);

11. Damaged, infected and treated at initial provision with Luxan Fungaflor EC, dosage 75 ml/ton of potatoes, followed by 3× a double dosage of Talent, viz. within 1 week after initial provision and after 6 and 12 weeks of storage (cells 13 and 21);

12. Damaged, infected and treated with Talent within 1 week after initial provision and after 6 and 12 weeks of storage (cells 17, 18, 21 and 28).

*=comparative example

Treatment with Fungicides

The treatments with the fungicide formulations to be tested, against the spread of silver scurf were carried out 1 day after the above-specified storage period. The treatments against Fusaria and Phoma were carried out in each case one day after the performance of the artificial damage and infection.

In the treatments the agents to be administered were distributed over the potatoes via a disk mister (type: Mafex 87A) mounted above a roller conveyor, using 1 liter of spraying liquid per 1000 kg of potatoes.

In the treatments with the different formulations and dosages the dosing position of the Mafex varied from 29.5 to 35.

During the treatments no problems arose with the product supply and discharge on the roller conveyor, there was always a neatly continuous potato bed, one tuber thick, on the roller conveyor and the distribution of the desired dosage on the tubers was splendid.

Treatments with Talent (Carvone)

Against the spread of silver scurf, treatments with Talent were carried out after:

4 days in cell 21 (350 ml) objects 10 and 12 and in cell 13 (700 ml) object 11;

49 days in cell 21 (350 ml) objects 4 through 10 and 12 and in cell 13 (700 ml) object 11;

81 days in cell 28 (350 ml) objects 4 through 10 and 12 and in cell 13 (700 ml) object 11.

For the control of *Fusarium solani* var. *coeruleum* and *Fusarium sulphureum*, treatments with Talent were carried out after:

0 days in cell 21 (350 ml) objects 10 and 12 and in cell 13 (700 ml) object 11;

42 days in cell 18 and 28 (350 ml) objects 4 through 10 and 12 and in cell 21 (700 ml) for object 11.

The planned treatment after 84 days (respectively, 2nd treatment for objects 4 through 9 and 3rd treatment for the objects 10 through 12) was omitted in view of sufficient differences in attack.

For the control of *Phoma exigua* var. *foveata*, treatments with Talent were performed after:

0 days in cell 17 (350 ml) objects 10 and 12 and in cell 13 (700 ml) obj. 11;

38 days in cell 17 (350 ml) objects 4 through 10 and 12 and in cell 13 (700 ml) obj. 11. The planned treatment after 90 days (respectively, 2nd treatment for objects 4 through 9 and 3rd treatment for the objects 10 through 12) was omitted in view of sufficient differences in attack.

The carvone content in the storage atmosphere was determined through adsorption of carvone to the adsorbent Tenax, followed by thermodesorption cold trap injection on the GC (gas chromatograph).

During the storage season, weekly air samples were taken in the storage cells. Depending on the expectable carvone concentration, for 15 to 60 seconds 1 ml of air/sec was sucked in through glass tubes filled with 100 mg Tenax TA (20–35 mesh). The air samples were taken at the top in the storage cells. On the treatment dates a sample was taken both prior to and about one hour after dosage. Samplings was carried out singly.

Prior to analysis of the loaded Tenax tubes, as an internal standard, 0.3 µl of a 1-methylnaphthalene solution in hexane was added (1-methylnaphthalene conc. 0.3 mg/l).

Fungicidal Action Against Silver Scurf

For the purpose of determining the initial attack of silver scurf, at the start of the tests, twelve samples of 25 tubers were collected and assessed. For an intermediate assessment, after 91 days, per treatment/agent/combination of agents and repeat, 25 tubers were collected at random. After 92 days these samples were washed and the tubers were assessed on one side for the occurrence of silver scurf. The final sampling occurred after 132 days. Depending on the tuber surface area covered with silver scurf, the tubers were categorized into classes. The following classes were distinguished:

| Class I   | –0%       | tuber surface affected - aver. 0%     |
|-----------|-----------|---------------------------------------|
| Class II  | 0–5%      | tuber surface affected - aver. 2.50%  |
| Class III | 5–12.5%   | tuber surface affected - aver. 8.75%  |
| Class IV  | 12.5–25%  | tuber surface affected - aver. 18.75% |
| Class V   | 25–50%    | tuber surface affected - aver. 37.50% |
| Class VI  | 50–75%    | tuber surface affected - aver. 62.50% |
| Class VII | 75–100%   | tuber surface affected - aver. 87.50% |

By multiplying the number of tubers in the different classes by the average percentage of affected tuber surface of the class in question, summing these products and dividing the total by the number of tubers assessed (25), per sample an average percentage of silver scurf attack was obtained.

Fungicidal Action Against *Fusarium Solani* var.*coeruleum*

The assessment for *Fusarium solani* var. *coeruleum* was carried out after 78 and 79 days. Here, too, for the variants and repeats in question, the total number of tubers and the number of tubers affected by the fungus specified were determined.

Fungicidal Action Against *Fusarium sulphureum* + and −

The assessment for these attacks was carried out after 80 and 81 days. Here, too, for the variants and repeats in question, the total number of tubers and the number of tubers affected by *Fusarium sulphureum* were determined.

Fungicidal Action Against *Phoma exigua* var.*foveata*

The assessment for Phoma attack occurred after 60 days. For the variants and repeats in question, the total number of tubers and the number of tubers affected by Phoma were determined.

Statistic Data Processing

To be able to determine if the agents/combinations differed reliably from each other and from the untreated potatoes with regard to the attack by different fungal diseases, a variance analysis was carried out, which yields an l.s.d. value (least significant difference). The averages of the agents/formulations differ significantly per disease, at a reliability of 95%, if their difference is greater than the l.s.d. value.

RESULTS

Storage

Ventilation, Temperature and Air Humidity

The eight storage cells used were equipped with fresh air cooling. These cells were also provided with electrical heating elements. Via heating and substantially internal ventilation, in all cells the desired temperature could be maintained during storage. To prevent an increase, if any, of the $CO_2$ concentration in the cells, some fresh air was regularly admixed. Temperature control proceeded via thermostats on the electrical heating elements. Temperature monitoring occurred via calibrated electronic reading equipment. During storage the temperatures aimed for could be properly maintained. The air humidity in the cells varied from 85 to 95%, viz. in the silver scurf cells from 90 to 95% and in the other cells from 85 to 90%.

Carvone Content in the Storage Atmosphere

Figure 2:
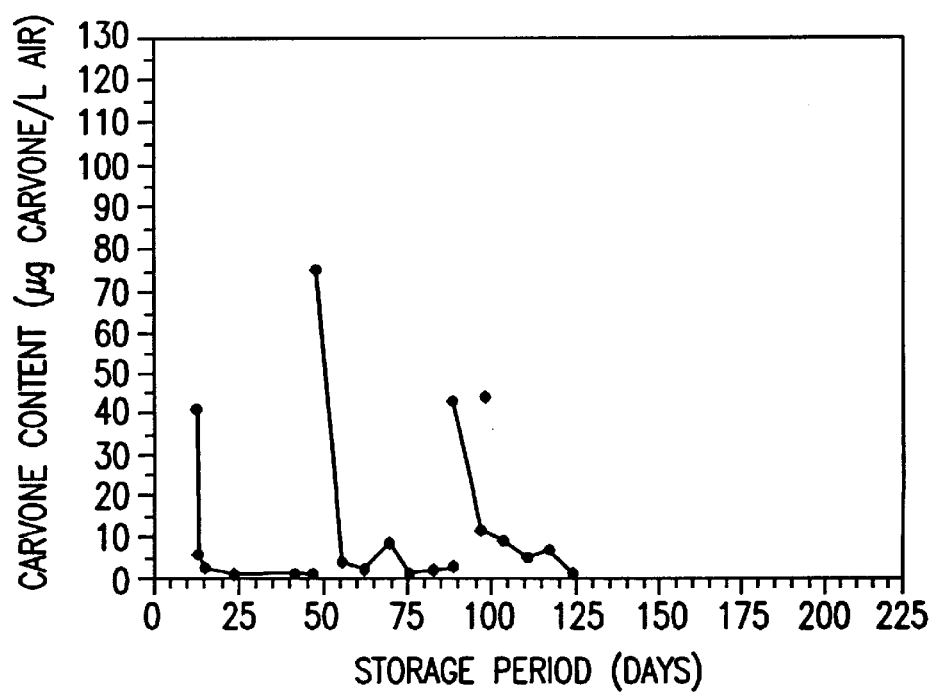
FIG. 2 is a graph showing the carvone content in air against storage period in storage cell 21.
Figure 3:
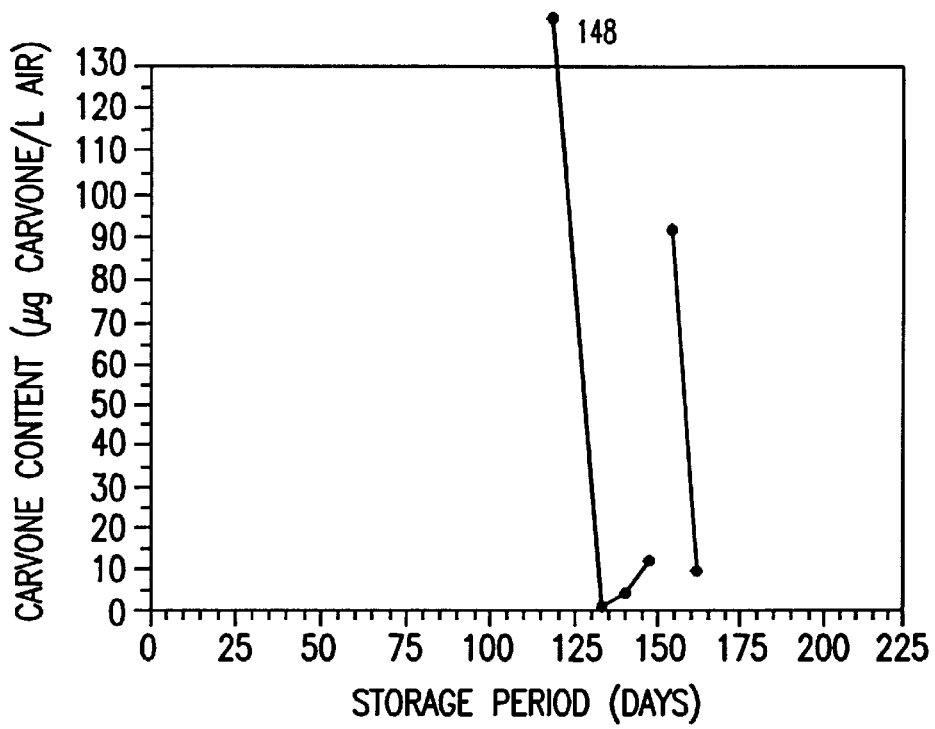
FIG. 3 is a graph showing the carvone content in air against storage period in storage cell 17.
Figure 4:
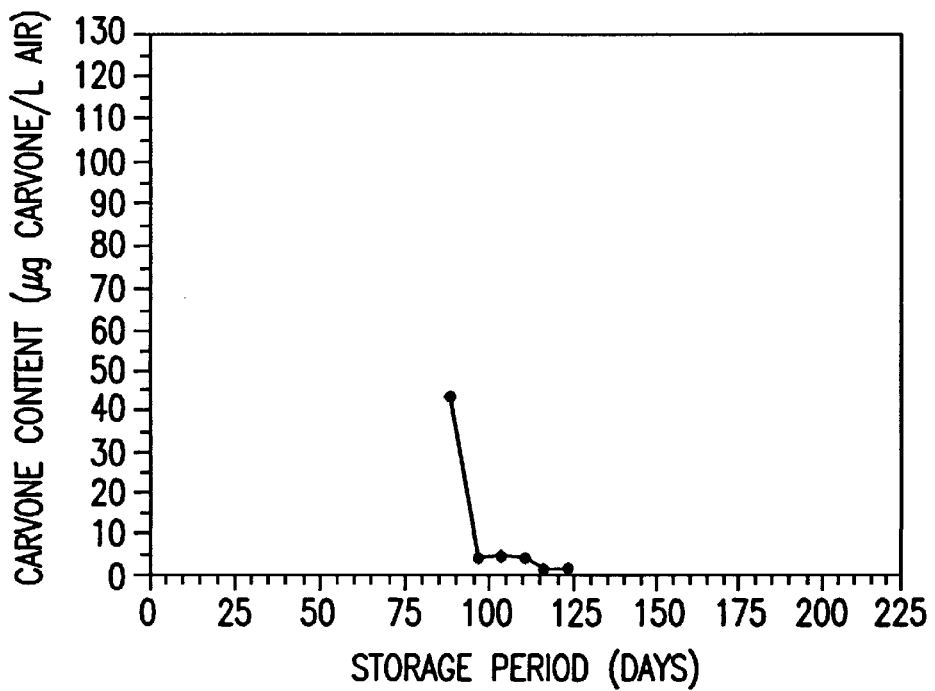
FIG. 4 is a graph showing the carvone content in air against storage period in storage cell 18.
Figure 5:
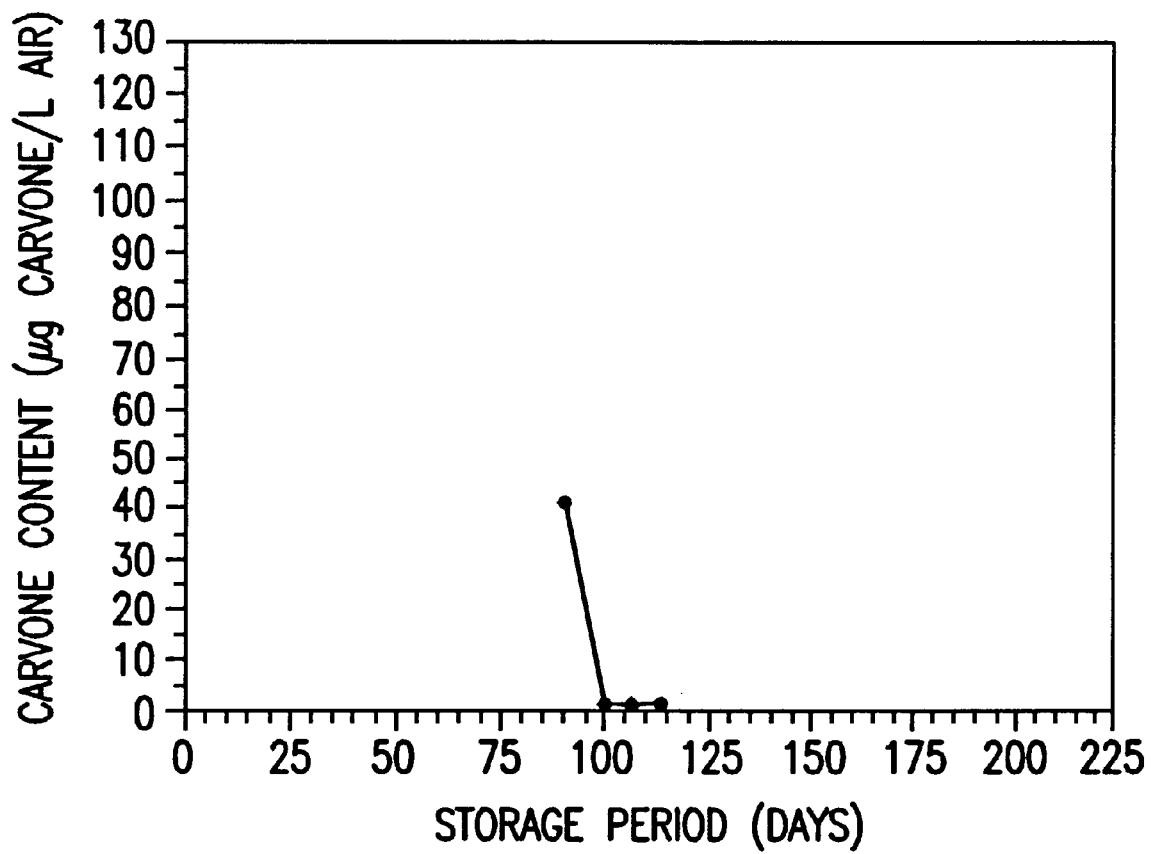
FIG. 5 is a graph showing the carvone content in air against storage period in storage cell 28.

The results of the measurements are shown in FIGS. 1–5. In all five cells, after the dosage with Talent (carvone), a rapid decrease in the carvone content occurred. On average, over the storage season, the carvone contents were rather low. Where a double dosage,was used, the concentration remained on average higher than with the normal dosage.

Fungicidal Action

Silver Scurf Attack

Table 1 summarizes the results of the intermediate measurements for silver scurf.

The initial silver scurf attack was, at initial provision, 3.975±1.0941.

From Table 1 it can be derived that after about 13 weeks of storage (just before the 2nd Talent treatment of the objects 4 through 9 and the 3rd treatment of the objects 10 through 12) all agents/combinations exhibit a significant controlling effect against silver scurf.

Mutual comparison shows that object 11 (Luxan Fungaflor EC and 2× a double dosage of Talent) exhibits the best controlling effect, immediately followed by object 9 (D4109 EC with 1× Talent).

Object 10 (Luxan Fungaflor EC with 2× Talent), object a (higher dosage of D4108 EC with 1× Talent), object 3 (1.5× higher dosage with Luxan Fungaflor EC), object 6 (D4112 EC+Luxan Fungaflor EC and 1× Talent) and object 7 (lower dosage of D4108 EC and 1× Talent) also exhibit a good controlling effect.

Compared to the objects already mentioned, the controlling effect of object 2 (normal dosage of Luxan Fungaflor EC), object 12 (2× Talent) and object 5 (higher dosage of D4112 EC and 1× Talent) lags behind somewhat. The action of object 4 (lower dosage of D4112 EC with 1× Talent) appears to be the least effective.

The results of the final assessment for silver scurf are summarized in Table 2.

TABLE 1

Attack by silver scurf after 92 days.

| Average % of tuber surface covered by silver scurf | Object no. | 11 | 9 | 10 | 8 | 3(*) | 6 | 7 | 2(*) | 12(*) | 5(*) | 4(*) | 1(*) |
|---|---|---|---|---|---|---|---|---|---|---|---|---|---|
| 2.9591 | 11 | | | | | | | | | | | | |
| 3.8870 | 9 | * | | | | | | | | | | | |
| 4.8375 | 10 | * | * | | | | | | | | | | |
| 5.0500 | 8 | * | * | | | | | | | | | | |
| 5.1750 | 3 | * | * | | | | | | | | | | |
| 5.8125 | 6 | * | * | * | * | | | | | | | | |
| 6.0577 | 7 | * | * | * | * | * | | | | | | | |
| 9.0188 | 2 | * | * | * | * | * | * | * | | | | | |
| 9.2625 | 12 | * | * | * | * | * | * | * | | | | | |
| 10.7904 | 5 | * | * | * | * | * | * | * | * | * | | | |
| 14.0745 | 4 | * | * | * | * | * | * | * | * | * | * | | |
| 21.8515 | 1 | * | * | * | * | * | * | * | * | * | * | * | |

LSD = 0.6498
(*) = comparative example
*indicate significant differences

TABLE 2

Attack by silver scurf after 134 days (final assessment).

| Average % of tuber surface covered by silver scurf | Object no. | 11 | 9 | 10 | 8 | 3(*) | 6 | 7 | 2(*) | 5(*) | 12(*) | 4(*) | 1(*) |
|---|---|---|---|---|---|---|---|---|---|---|---|---|---|
| 3.7750 | 11 | | | | | | | | | | | | |
| 4.8894 | 9 | * | | | | | | | | | | | |
| 5.9250 | 10 | * | * | | | | | | | | | | |
| 5.9875 | 8 | * | * | | | | | | | | | | |
| 6.5875 | 3 | * | * | * | * | | | | | | | | |
| 7.0750 | 7 | * | * | * | * | | | | | | | | |
| 7.1625 | 6 | * | * | * | * | * | | | | | | | |
| 10.0750 | 2 | * | * | * | * | * | * | * | | | | | |
| 10.9125 | 5 | * | * | * | * | * | * | * | * | | | | |
| 11.1000 | 12 | * | * | * | * | * | * | * | * | | | | |
| 16.3125 | 4 | * | * | * | * | * | * | * | * | * | * | | |
| 50.4530 | 1 | * | * | * | * | * | * | * | * | * | * | * | |

LSD = 0.5171
(*) = comparative example
*indicate significant differences

In the final assessment too, all agents/combinations appear to exhibit a significant controlling effect against silver scurf.

A mutual comparison of effects of the different treatments/combinations reveals that object 11 (Luxan Fungaflor EC and 3× a double dosage of Talent) gives the best controlling effect. As to effectiveness, this object is immediately followed by object 9 (D4109 EC followed by 2 Talent treatments).

The controlling effect of object 10 (normal dosage of Luxan Fungaflor EC followed by 3× Talent) and object 8 (higher dosage of D4108 EC, followed by 2× Talent) is comparable and good.

The controlling effect of object 3 (1.5× higher dosage of Luxan Fungaflor EC) and object 7 (lower dosage of D4108 EC, followed by 2× Talent) is comparable and can be qualified good.

Further, the controlling effect of object 6 (D4112 EC+Luxan Fungaflor EC, followed by 2× Talent) and object 7 can also be qualified as comparable and good.

Furthermore, the controlling effect of object 2 (normal dosage of Luxan Fungaflor EC) is found to be reliably better than that of object 5 (higher dosage of D4112 EC, followed by 2× Talent) and object 12 (3× Talent).

The least effective of all agents/combinations, finally, is object 4 (lower dosage of D4112 EC, followed by 2× Talent).

*Fusarium solani* var. *coeruleum* Attack

In Table 3 the results of the measurements regarding attack by *Fusarium solani* var. *coeruleum* are summarized.

Table 3 shows that with the exception of objects 2 and 3 (2 dosages of Luxan Fungaflor EC) all other agents/combinations exhibit a significant activity against *Fusarium solani* var. *coeruleum*.

Mutual comparison of the activity of the agents/combinations shows that object 11 (Luxan Fungaflor EC, followed by 2× a double dosage of Talent) gives by far the best controlling effect.

Of the other objects the controlling effect is less clear. The best results are scored here by object 6 (D4112 EC +Luxan Fungaflor EC and 1× Talent), followed, in terms of results, by the objects 8 and 7 (2 dosages of D4108 EC and 1× Talent). Next, the two dosages of D4112 EC, followed by 1× Talent (obj. 5 and 4) are found to exhibit better activity than D4109 EC, followed by 1× Talent (obj. 9). Luxan fungaflor EC, followed by 2× Talent (object 10) and 2× Talent alone (object 12) exhibit the least activity.

TABLE 3

Attack by *Fusarium solani* var. *coeruleum* after 78 and 79 days.

| Average % of tubers affected by *Fusarium solani* | Object no. | 11 | 6 | 8 | 7 | 5(*) | 4(*) | 9 | 10 | 12(*) | 3(*) | 2(*) | 1(*) |
|---|---|---|---|---|---|---|---|---|---|---|---|---|---|
| 0.4577 | 11 | | | | | | | | | | | | |
| 33.2551 | 6 | * | | | | | | | | | | | |
| 36.8685 | 8 | * | * | | | | | | | | | | |
| 38.9499 | 7 | * | * | * | | | | | | | | | |
| 40.6612 | 5 | * | * | * | * | | | | | | | | |
| 41.2594 | 4 | * | * | * | * | | | | | | | | |
| 43.3129 | 9 | * | * | * | * | * | * | | | | | | |
| 46.1805 | 10 | * | * | * | * | * | * | * | | | | | |
| 49.9334 | 12 | * | * | * | * | * | * | * | * | | | | |
| 78.1109 | 3 | * | * | * | * | * | * | * | * | * | | | |
| 78.6097 | 2 | * | * | * | * | * | * | * | * | * | | | |
| 78.6422 | 1 | * | * | * | * | * | * | * | * | * | | | |

LSD = 1.2952
(*) = comparative example
*indicate significant differences

*Fusarium sulphureum*+ Attack (Resistant to Thiabendazole)

In Table 4 the results of the measurements on attack by *Fusarium sulphureum*+ are summarized.

Table 4 shows that all agents/combinations exhibit a significant activity against *Fusarium sulphureum*+.

Mutual comparison of the activity of the agents/combinations shows that the controlling effect of object 11 (Luxan Fungaflor EC and 2× a double dosage of Talent) is by far the greatest.

Next to be rated most effective are object 9 (D4109 EC and 1× Talent) and object 8 (higher dosage of D4108 EC and 1× Talent). Then the objects 7 (lower dosage of D4108 EC and 1× Talent) and 10 (Luxan Fungaflor EC and 2× Talent) can still be qualified as having a fairly good activity.

To be qualified clearly as least effective are object 5 (higher dosage of D4112 EC and 1× Talent), object 12 (2× Talent) and in particular object 4 (lower dosage of D4112 EC and 1× Talent).

TABLE 4

Attack by *Fusarium sulphureum* + after 80 and 81 days.

| Average % of tubers affected by *Fusarium sulphureum* + | Object no. | 11 | 9 | 8 | 7 | 10 | 3(*) | 6 | 2(*) | 5(*) | 12(*) | 4(*) | 1(*) |
|---|---|---|---|---|---|---|---|---|---|---|---|---|---|
| 2.4951 | 11 | | | | | | | | | | | | |
| 9.4974 | 9 | * | | | | | | | | | | | |
| 10.1217 | 8 | * | | | | | | | | | | | |
| 14.1231 | 7 | * | * | * | | | | | | | | | |
| 16.1122 | 10 | * | * | * | * | | | | | | | | |
| 21.8768 | 3 | * | * | * | * | * | | | | | | | |
| 26.2313 | 6 | * | * | * | * | * | * | | | | | | |
| 26.8985 | 2 | * | * | * | * | * | * | | | | | | |
| 45.8276 | 5 | * | * | * | * | * | * | * | * | | | | |
| 46.7307 | 12 | * | * | * | * | * | * | * | * | | | | |
| 59.7406 | 4 | * | * | * | * | * | * | * | * | * | * | | |
| 69.7572 | 1 | * | * | * | * | * | * | * | * | * | * | * | |

LSD = 0.9457
(*) = comparative example
*indicate significant differences
*Fusarium sulphureum* - attack (not resistant to thiabendazole)

In Table 5 the results of the measurements on attack by *Fusarium sulphureum*− are summarized.

TABLE 5

Attack by *Fusarium sulphureum* - after 80 and 81 days.

| Average % of tubers affected by *Fusarium sulphureum* – | Object no. | 9 | 8 | 11 | 7 | 6 | 3(*) | 2(*) | 10 | 12(*) | 5(*) | 4(*) | 1(*) |
|---|---|---|---|---|---|---|---|---|---|---|---|---|---|
| 1.7570 | 9 | | | | | | | | | | | | |
| 1.8738 | 8 | | | | | | | | | | | | |
| 2.2962 | 11 | | | | | | | | | | | | |
| 4.8217 | 7 | * | * | * | | | | | | | | | |
| 14.2680 | 6 | * | * | * | * | | | | | | | | |
| 16.4422 | 3 | * | * | * | * | * | | | | | | | |
| 19.5182 | 2 | * | * | * | * | * | * | | | | | | |
| 22.0268 | 10 | * | * | * | * | * | * | * | | | | | |
| 25.8261 | 12 | * | * | * | * | * | * | * | * | | | | |
| 36.4681 | 5 | * | * | * | * | * | * | * | * | * | | | |
| 56.4031 | 4 | * | * | * | * | * | * | * | * | * | * | | |
| 72.1372 | 1 | * | * | * | * | * | * | * | * | * | * | * | |

LSD = 0.7864
(*) = comparative example
*indicate significant differences

Table 5 shows that all agents/combinations also have a significant activity against *Fusarium sulphureum-*.

Mutual comparison of the activity of the agents/combinations shows that object 9 (D4109 EC and 1× Talent), object 8 (higher dosage D4108 EC and 1× Talent) and object 11 (Luxan Fungaflor EC and 2× double dosage of Talent) give the best controlling effect. Object 7 too (lower dosage of D4108 EC and 1× Talent) exhibits a very good activity.

The controlling effect of Luxan Fungaflor EC alone (objects 2 and 3) is better than that of the combination of Luxan Fungaflor EC and 1× Talent (object 10). Finally, it can be noted that the treatments with agents that contain carvone alone (objects 4, 5 and 12) show a less effective controlling result.

Attack by *Phoma exigua* var. *foveata*

In Table 6 the results of the measurements on *Phoma exigua* var. *foveata* are summarized.

and 2× Talent) to be the most effective. The next best score is that of the formulation D4108 EC with 1× Talent (objects 8 and 7).

Next in line, in terms of controlling effect, are object 6 (D4112 EC +Luxan Fungaflor EC and 1× Talent), object 9 (D4109 EC and 1× Talent) and object 11 (Luxan Fungaflor EC and 2× a double dosage of Talent).

The activity of treatments with carvone alone (objects. 4, 5 and 12) and imazalil alone (objects 2 and 3) was clearly less effective.

What is claimed is:

1. A sprout inhibiting and anti-fungal composition for potatoes, comprising synergistic effective amounts of the combination of carvone and imazalil.

2. A composition according to claim 1, further comprising a suitable carrier.

TABLE 6

Attack by *Phoma exigua* var. *foveata* after 60 days.

| Average % of tubers affected by Phoma | Object no. | 10 | 8 | 7 | 6 | 9 | 11 | 12(*) | 3(*) | 5(*) | 2(*) | 4(*) | 1(*) |
|---|---|---|---|---|---|---|---|---|---|---|---|---|---|
| 15.7021 | 10 | | | | | | | | | | | | |
| 28.5433 | 8 | * | | | | | | | | | | | |
| 30.3914 | 7 | * | * | | | | | | | | | | |
| 35.5336 | 6 | * | * | * | | | | | | | | | |
| 38.4544 | 9 | * | * | * | * | | | | | | | | |
| 41.0350 | 11 | * | * | * | * | * | | | | | | | |
| 54.9223 | 12 | * | * | * | * | * | * | | | | | | |
| 64.0668 | 3 | * | * | * | * | * | * | * | | | | | |
| 71.1260 | 5 | * | * | * | * | * | * | * | * | | | | |
| 75.6513 | 2 | * | * | * | * | * | * | * | * | * | | | |
| 79.9465 | 4 | * | * | * | * | * | * | * | * | * | * | | |
| 95.4509 | 1 | * | * | * | * | * | * | * | * | * | * | * | |

LSD = 1.3279
(*) = comparative example
*indicate significant differences

Table 6 shows that all agents/combinations have a significant activity against *Phoma exigua* var. *foveata*.

A mutual comparison of the activity of the different agents/combinations shows object 10 (Luxan Fungaflor EC 3. A composition according to claim 1, wherein the composition is in the form of a solution, granules, a paste, an emulsion, a suspension, a suspo-emulsion or a powder.

4. A composition according to claim 1, wherein the composition further comprises suitable solvents, fillers or other agents conventionally present.

5. A composition according to claim 1, wherein the composition is an emulsion in water or in an aqueous solution.

6. A composition according to claim 1, comprising 400–600 g/l carvone and 50–250 g/l imazalil.

7. The composition according to claim 1, wherein the weight ratio of imazalil to carvone is 1:1 to 1:10.

8. A method for inhibiting sprouting in potatoes and inhibiting fungi, comprising treating potatoes with synergistic effective amounts of carvone and imazalil.

9. A method according to claim 8, wherein the treating is by misting, spraying, atomizing, scattering or evaporating.

10. The method according to claim 8, wherein the fungi is selected from the group consisting of *Helminthosporium solani, Phoma exigua* var. *exigua, Phoma exigua* var. *foveata, Fusarium sulphureum, Fusarium solani Fusarium* solani *Fusarium solani var. coeruleum, Phytophthora erythroseptica* and combinations thereof.

* * * * *